(12) United States Patent
McClain et al.

(10) Patent No.: US 8,326,413 B1
(45) Date of Patent: Dec. 4, 2012

(54) METHOD AND DEVICE FOR DETERMINING TOOTH STATUS UNDERNEATH A CROWN

(76) Inventors: Maxine McClain, Atlanta, GA (US); J. Bruce McClain, Lovettsville, VA (US)

( * ) Notice: Subject to any disclaimer, the term of this patent is extended or adjusted under 35 U.S.C. 154(b) by 0 days.

(21) Appl. No.: 13/314,955

(22) Filed: Dec. 8, 2011

(51) Int. Cl.
*A61B 5/05* (2006.01)
*A61C 13/00* (2006.01)
*A61C 5/00* (2006.01)

(52) U.S. Cl. .......................... 600/547; 433/167; 433/215

(58) Field of Classification Search .................. 600/547, 600/548; 433/167, 215, 218
See application file for complete search history.

(56) References Cited

U.S. PATENT DOCUMENTS

| | | |
|---|---|---|
| 4,215,698 A | 8/1980 | Nuwayser |
| 5,033,999 A | 7/1991 | Mersky |
| 5,695,339 A | 12/1997 | Abere |
| 6,090,053 A | 7/2000 | Ruetschi et al. |
| 6,230,050 B1 | 5/2001 | Pitts et al. |
| 6,866,509 B2 | 3/2005 | Jensen |
| 6,997,883 B1 | 2/2006 | Hahn |
| 2006/0167372 A1 | 7/2006 | Kusano |
| 2009/0035723 A1 | 2/2009 | Daniel et al. |
| 2010/0143861 A1 | 6/2010 | Gharib et al. |
| 2010/0152579 A1 | 6/2010 | Lin et al. |

OTHER PUBLICATIONS

Liao et al., In situ tracing the process of human enamel demineralization by electrochemical impedance spectroscopy (EIS), Journal of Dentistry 35 (2007), pp. 425-430, 2006, Elsevier Ltd.
Sword et al., Use of Electrochemical Impedance Spectroscopy to Evaluate Resin-Dentin Bonds, Journal of Biomedical Materials Research Part B: Applied Biomaterials, pp. 468-77, 2007, Wiley Periodicals, Inc.
Wadgaonkar et al., Evaluation of the effect of water-uptake on the impedance of dental resins, Biomaterials 27, pp. 3287-294, 2006, Elsevier Ltd.
Longbottom et al., Detection of dental decay and its extent using a.c. impedance spectroscopy, Nature Medicine, vol. 2, No. 2, pp. 235-37, 1996, Nature Publishing Group.
Chang et al., A self-adaptive fluidic probe for electrical caries detection, Biomed Microdevices 10, pp. 447-57, 2008, Springer Science + Business Media, LLC.

*Primary Examiner* — Max Hindenburg
*Assistant Examiner* — Jonathan M Foreman
(74) *Attorney, Agent, or Firm* — Wyatt, Tarrant & Combs, LLP; William S. Parks

(57) ABSTRACT

An apparatus and method for the detection of dental caries on the surface of a remaining tooth present underneath a crown are provided. Such an inventive concept involves the utilization of a proper electrically conductive pathway from the crown exterior to the tooth itself, allowing for impedance measurements to be undertaken to determine the degree of potential demineralization within the tooth and/or adhesive loss at the tooth/crown interface, all due to decay attributable to dental caries or like problems. In such a manner, a measuring electrode may be applied to a specific point on the target crown as well as on the adjacent gum, to measure impedance levels for any appreciable decreases which would indicate underlying tooth decay exists. The dental professional may then undertake proper therapeutic measures to treat such tooth locations in order to avoid far more expensive repairs, such as the implementation of bridges or implants.

1 Claim, 1 Drawing Sheet

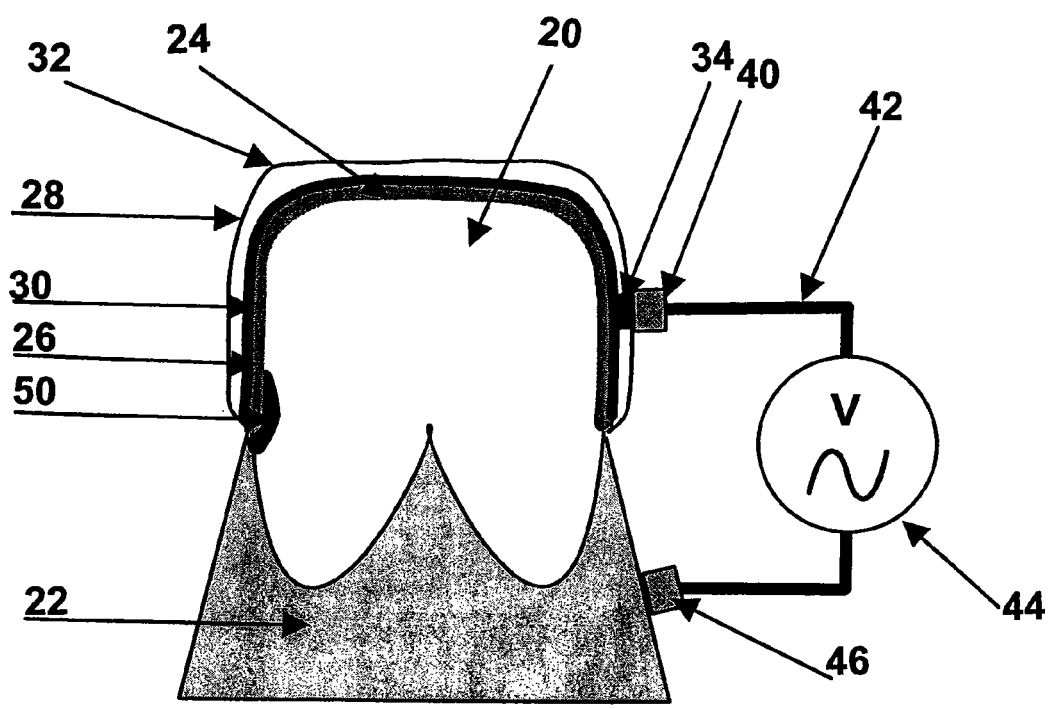

METHOD AND DEVICE FOR DETERMINING TOOTH STATUS UNDERNEATH A CROWN

FIELD OF THE INVENTION

The present invention relates to an apparatus and method for the detection of dental caries on the surface of a remaining tooth present underneath a crown. Such an inventive concept involves the utilization of a proper electrically conductive pathway from the crown exterior to the tooth itself, allowing for impedance measurements to be undertaken to determine the degree of potential demineralization within the tooth and/or adhesive loss at the tooth/crown interface, all due to decay attributable to dental caries or like problems. In such a manner, a measuring electrode may be applied to a specific point on the target crown, as well as on the adjacent gum (or other part of a patient's body), to measure impedance levels for any appreciable decreases which would indicate underlying tooth decay has been initiated. From that point, the dental professional may undertake proper therapeutic measures to treat such tooth locations in order to avoid far more expensive repairs, such as the implementation of bridges or implants. The method of providing an effective crown system to permit such electrical impedance measurements, as well as the entire adhesive/crown composite applied to a properly modified base tooth, are also encompassed within this invention.

BACKGROUND OF THE INVENTION

Dental crowns have been utilized for many years to provide protection to teeth that have required substantial, but not complete, removal due to various problems, such as the development of deleterious cracks at the subject tooth surface. Without removal of the affected tooth portion, the chances for bacterial infection (and thus invasive dental caries) within the outer tooth portion may create further complications that would consequently lead to extensive dental repairs. Additionally, the entire removal of the affected tooth could lead to expensive bridge or implant work that, furthermore, could be rather cumbersome, if not painful, at least initially, to the target patient. As well, the potential for root damage or destruction without proper treatment of an affected tooth may create highly painful circumstances for which the patient would require invasive dental repairs to overcome. As such, a dentist has typically adhered such a metal and/or ceramic crown directly over an affected tooth or, alternatively, has ground down an affected tooth until a residual post remains of sufficient size and strength to receive and retain (again with the aid of adhesives) crowns of similar materials. In such a manner, the patient may enjoy the retention of the base tooth, while also having the benefit of an artificial implement that is properly molded to fit in complementary fashion to the remaining tooth structure, as well as to provide the same shape (and sometimes, color) as the removed tooth portion from an outward appearance. Crowns have been perfected to the point that proper occlusion of such structures may be configured as closely to that of the original tooth in relation to the adjacent teeth in order for the target patient to, again, enjoy substantially the same benefits of the look and function of the prior tooth. Hence, dental crowns have become a standard and effective replacement for affected teeth without the necessity of full tooth removal and thus potentially more cumbersome and/or expensive alternatives.

One significant downside to crown technology, however, is, basically, the lack of transparency for a dental professional to have a proper vantage point to visibly examine the underlying tooth throughout the time such a crown is present. In other words, although a crown will provide a certain degree of protection to the underlying post, there still exists a definite possibility that undesirable bacteria or other microorganisms may penetrate underneath the crown and its adhesive layer (covering the subject tooth post) (or, alternatively, may have resided on or within the covered tooth surface prior to crown implementation) and begin to cause demineralization and/or adhesive decomposition as a result. In such a situation, without any capability to properly analyze the underlying tooth for any such problems, the dental professional would have no effective way of assessing the tooth status in terms of potential decay or other loss in tooth and/or crown integrity. If the tooth suffers from dental caries, for instance, the crown may lose its adhesive potential to the tooth surface as such a surface would potentially deteriorate over time, effectively altering the post structure upon which the crown has been situated. Additionally, beyond the potential for crown movement or loss, the underlying tooth may, without proper therapeutic action taken to disinfect and/or reverse such a caries problem, suffer a loss of stability itself, which may lead to tooth decay outright, or even to destruction or, at least, compromise some extent of the root. In any event, the results of such undesirable underlying tooth caries would undoubtedly lead to far more expensive, cumbersome, and potentially painful results for the target patient. Avoidance of such end results would thus be of great interest to the dental professional as knowledge of underlying tooth decay of such sort would at least provide an avenue for treatment to be undertaken. As it stands today, however, there are no effective measures available for detection of sub-crown tooth decay to overcome such an institutional deficiency.

Generally speaking, within the dental field, caries is defined as the progressive decay of tooth or bone. Dental caries, itself, may be treated through the removal of decayed (or decaying) material in the subject tooth and filling the resultant space with a dental amalgam or polymer, in essence to retain as much of the target tooth structure as possible. In more severe cases, if such decay has progressed too far, complete removal of the entire tooth may be employed. As such, early diagnosis of dental caries is of utmost importance to best guarantee the subject tooth could be properly treated in order to avoid tooth removal.

Historically, as noted above, visual diagnosis of dental caries has been undertaken by dental professionals. More recently, mechanical, radiographic, and electric probes have been utilized for such purposes as well. Despite the potential for clear visual identification of affected areas, in certain situations caries is not easy to find. For instance, decay on the approximal surface of a tooth resulting from plaque on the inter-dental spaces may not be detected by simple visual actions, or, for that matter, through mechanical probing and prodding of a subject tooth, since the approximal surfaces may not be easily seen nor easily reached by a probe. Hence, the development of certain electrical devices to provide effective measurements of tooth surface stability upon direct exposure thereto has permitted more reliability in caries diagnosis over and above strict visual acts, even when accompanied by tactile examination utilizing a common mechanical probe. Such electrical probes involve direct exposure to a tooth surface to measure any potential impedance of electrical signals throughout a tooth's structure. A change in the impedance value in the path of the electrical signal across the tooth would be a fair indication of onset of decay, thus providing a reliable measure of decay on which to make a proper diagnosis of dental caries. Such newer electrical probes have thus been proven to provide effective means to aid patients with early diagnosis of such problems when actually examined and, more succinctly, in terms of actual exposed (i.e., uncovered) teeth.

Furthermore, in terms of potential diagnosis of such caries problems, even if such dental examinations are not performed regularly on a target patient, such a person may provide a self-diagnosis through the existence of localized pain (or perhaps an increase in such pain at such a specific location) due to the presence of decaying material. Such a painful result, however, will most likely occur specifically because of direct exposure to outside elements. In any event, such visual identification, mechanical and/or electrical probing, and pain results all require the lack of any effective covering over a subject tooth, such as a crown, in order to permit proper caries diagnosis.

Clearly, visual identification of decay is impossible if the subject tooth structure is completely covered by a crown. Likewise, mechanical probing and pain indications would not be of much use as the same visual limitations exist for mechanical issues, and a patient may not suffer the same pain maladies since a crown would prevent external stimuli from causing undesirable reactions within the decaying tooth material to accord such a result. Additionally, however, the effectiveness of electrical impedance measurements as of today for determining tooth surface conditions is limited to, again, teeth that are properly exposed for such procedures, as well as the lack of a covering (such as, of course, a crown) that typically constitutes a material that will not permit effective electrical signals to be measured for such a purpose. Without access to the region susceptible to decay (i.e. via a specially designed crown) the possibility of diagnosing an underlying surface or structure within a crowned tooth has not been available within the dental field.

Additionally, the utilization of radiographic and/or X-ray procedures to properly diagnose caries potential under a crown is rather limited, either due to the crown material effecting the overall capability of the scan in question, or the difficulty in determining such a possible slight demineralization occurrence within an underlying tooth surface with such analytical methods. Basically, dental radiographs performed to detect dental caries merely show density differences in tooth structure caused by loss of calcium. As such, this method is limited in caries detection on the two accessible side surfaces of teeth. The remaining structures, particularly the occlusal, i.e. biting, surface, frequently develop considerably large carious lesions that remain undetectable by radiographic examination. These devices thus typically fail to detect a cavity until an advanced stage, and therefore are not good for early detection and treatment. Furthermore, X-ray, etc., devices are not only static by nature in terms of location, but they are also expensive to utilize. As well, such devices may expose a patient to the harmful exposure of radiation in such circumstances. Although such procedures are rather typical during dental examinations, they are still undesirable in the long run, and, again, are severely limited in their actual usefulness for caries diagnosis, particularly for sub-crown tooth structures.

As such, all of these alternative methods for caries detection have significant drawbacks and/or are limited in their capabilities to the detection of caries potential on exposed tooth surfaces. The presence of a dental crown prevents effective caries detection such that, as of today, the dental industry has not accorded any manner of compensating for such a situation, short of actually removing the crown itself. Of course, such an action is undesirable as continued removal and replacement of a crown will likely affect the dimensional stability of the remaining tooth, require further application of potentially harmful adhesives within a patient's oral cavity, and, most importantly, would prove to be rather expensive.

Thus, there exists a specific need to permit proper diagnosis of problems with teeth that are covered with crowns, particularly in terms of any potential disease or undesirable condition that may lead to crown or tooth removal if not properly treated timely. A method and device, thus, that would provide an effective means of detecting underlying tooth structure problems underneath a crown would be very important within the dental field to permit early diagnosis of potential decay problems in order to alleviate any need to undergo consequential surgical and/or implant procedures due to extensive unknown underlying tooth damage. To date, again, the dental field lacks such a beneficial method and device.

ADVANTAGES AND SUMMARY OF THE INVENTION

It is thus one significant advantage of this invention is that it provides a noninvasive method of determining the presence and degree of demineralization and decay of an underlying tooth structure under a crown. Another advantage of this invention is the capability of providing a new type of crown adhesive material to permit avoidance of crown/material interference with electrical signals to allow for proper impedance measures to be made for underlying tooth structure analysis, or even to enhance the magnitude of the impedance change that is measured with the onset of decay to the tooth structure.

Accordingly, this invention encompasses a method of detecting tooth surface deficiencies for a tooth covered by a crown including metal constituents therein, wherein said method includes the provision of an original tooth structure present within a target patient's oral cavity, said tooth structure having present, there over, a crown structure, wherein said crown structure is adhered to said tooth structure through the utilization of an adhesive, wherein said adhesive is sufficiently strong to hold said crown structure in place over said tooth structure such that the overall configuration accorded by such a crown structure to the patient is substantially similar to the over configuration of the tooth structure prior to inclusion of such a crown structure and wherein said crown structure is rigidly adhered to said tooth structure without any noticeable and undesirable movement, and wherein said crown structure includes a port component therein that permits integration on a temporary and selective basis of an externally applied electrode that couples to the crown in such a way that the impedance of the underlying tooth is accessible to the externally applied electrode without any interference by the material composing the crown; said method further including the integration of an electrode within said port on one end and contact with another part of the target patient's body on the other end; and, operating said electrode to measure the degree of electrical impedance through the underlying tooth structure such that said impedance measurements will indicate the degree and location of any demineralization or other tooth surface alteration that is associated with dental caries. The overall device, including the modified crown to include a suitable port for electrode integration, as well as, alternatively, a proper electrically conductive lining separating the crown and an adhesive that may include a crystalline salt that may cause demineralization of the adhesive upon the presence of sufficient bacteria growth between the tooth and the crown, while still providing sufficient adhesive properties to accord proper retention of the crown over said tooth surface, is also encompassed within this invention.

As noted above, electrical impedance measurements have been utilized for the detection of decay in and on exposed tooth surfaces. These past devices generally comprise a probe having a first, probe electrode which is placed in contact with the tooth to be tested, and a second, counter electrode separate from the probe electrode which is placed in contact with another part of the body of the patient (such as the gingiva or oral mucosa, as examples) in order to complete an electrical circuit connecting the two electrodes. Alternating electric current of fixed frequency, or over a known frequency range, is then passed through the tooth and any impedance levels are measured in order to correlate to the extent of possible caries present therein. Such a method requires, however, direct exposure to a tooth surface, for obvious reasons.

It is evident, however, that lack of transparency and/or proper electrical conductivity levels of typical metal/ceramic crowns prevents, as alluded to above, the capability of detecting any definitive status of an underlying tooth without removal thereof first. Thus, although prior impedance methods have been followed in the past to detect dental caries, the utilization of such probes in conjunction with crowns has not yielded any beneficial results at all. In essence, the typical crown structure and format militates against noninvasive detection of caries or other possible tooth damage in such a manner.

Thus, the invention described herein provides the first reliable method of overcoming such obstacles through a unique combination of properly designed crown materials and a properly formulated dental cement with, furthermore, a proper electrically conductive lining between the crown and the cement, all placed over an affected tooth structure. The crown may still utilize the same metallic and/or ceramic materials that accord proper tooth protections, as well as potential for the same basic function and appearance of the preceding tooth. However, a significant modification to such standard structures is the inclusion of a port component to which an electrode (or mini-electrode, as the case may be) can be attached (or possibly inserted) in order to allow for impedance measurements to be made through or at least sufficiently deep into the crown surface in order to best avoid contact with the metallic constituents of the crown itself. Conventional crown designs (not including any type of port of such nature) would create signal dissipation and/or interference upon the introduction of an electrode thereto, effectively rendering any impedance measurements unreliable. To date, there have been no crown designs that have included any access port for such a purpose. Hence, the base utilization of a properly configured crown structure to include such a necessary port provides a previously unavailable improvement over the prior art.

The crown exterior or the crown itself should be constructed from high-impedance, high-strength material (such as, one non-limiting examples, dielectric materials such as zirconia, aluminum oxide, and combinations thereof, at least) in order to reduce any potential for interference with the electrode measurements of electrical signal transfer through to the tooth surface. Importantly, as noted above, the crown will include a conductive port in at least one location on its surface. Such a port may be of a proper construction to permit not only proper protection to the subject tooth when the crown is present, but also to allow for transfer of electrical signals there through to the interior lining (if present) and ultimately to the subject tooth. To that end, the preferable configuration for such a port is actually a distinct area within the crown that is made from highly conductive material and that permits proper attachment of an electrode thereto with complete connection of the electrode to the conductive region of the crown surface alone. This port component may thus be produced as a plug to be introduced within a proper cutout of the crown (and that would reach from the exterior of the crown to the adhesive or, alternatively, the interior conductive lining present between the crown and the adhesive) and that is permanently attached therein. In essence, the port in such an embodiment would be a separate conductive region of the crown while the remainder of the crown is substantially non-conductive, allowing for electrode placement for direct conductive relation to the subject covered tooth surface to permit proper impedance measurements solely from the tooth surface (with minimal interference, at best, from the adhesive and any minimal contact with the non-port crown surface).

Furthermore, even with the presence of an electrode connected in some manner to a crown surface, there still remains the potential to apply a proper electrically conductive lining over the interior surfaces of such a crown to accord a low-impedance shell over the tooth and under the crown itself in order to further minimize the effect of the port location relative to the site of any possible decay. To that end, the inner lining must not only provide such an electrically conductive property, but must also not react with any other components utilized in the construction of the overall crown/tooth composite, nor with any typical fluids present within the target patient's oral cavity. Such a material may thus be of any of the precious metals (gold, silver, platinum, for instance) or any other like metallic compound that accords the same beneficial properties noted above. Certain materials may also provide a basis of anti-bacterial activity to provide some degree of protection to the underlying tooth when in place, at least in terms of reducing the chances of bacteria invasion from an external source through the multiple layers leading to the tooth surface. Such a conductive lining also aids in terms of greater reliability of impedance measurements for a situation wherein the electrode port is located any distance from the actual location of potential tooth decay. With the increase in conductivity provided between the tooth surface and the exterior of the subject crown through the presence of such a lining, any measured impedance of electrical signal would thus be attributable primarily to the presence of tooth decay (or possibly demineralization of the tooth surface leading to cement/adhesive degradation). Without such a low-impedance lining, there may be suspect results as to the measured levels of impedance throughout the overall crown/tooth composite due to the crown materials themselves. Thus, although such a lining is considered alternative as a component of the overall method and measuring device, it should be understood that its presence contributes greatly to the reliability and ultimate usefulness of the inventive system.

The adhesive component is of great importance, as well, primarily because of the necessity to the target patient for reliability in consistent crown retention. A loose crown would create noticeable problems for the patient, in other words, that would require dental professional attention. In any event, the adhesive (or cement) may be of any standard type that provides highly effective attachment means for a crown to the subject tooth structure. Removal of the crown would thus require a certain degree of dissolution or disengagement of the adhesive which would ultimately require reapplication of the same or another adhesive upon return of the crown to the subject tooth structure. Although there is no requirement for constituent within such an adhesive/cement formulation beyond that which accords such a high degree of temporary attachment, other components may be included within the adhesive/cement formulation to provide extra benefits in terms of bacterial presence under the crown. For instance, such a formulation may include a pH sensitive particulate salt (such as calcium carbonate) or other like substance (such as hydroxyapatite) that will cause the demineralization of the adhesive/cement when exposed to acidic waste byproducts of bacteria. In this manner, upon such demineralization, the adhesive will lose its integrity thus providing a low-impedance pathway from the site of decay to the crown (and thus on to the soft tissue on which the other electrode has been placed in contact with). Importantly, such an adhesive/cement should be sufficiently thin, generally, to not form an insulative barrier between the crown and the tooth surface (and thus the site of tooth decay). As such, the actual thickness of such an adhesive layer should be between 0.01 and 0.1 mil, generally, although a thicker layer may be employed as long as, again, such a layer will not insulate and thus impede electrical signal transfer, in order to ensure the impedance measurements provided by the crown-port located electrode will be reliable and not artificially embellished due to such an adhesive layer.

The electrodes utilized for the overall impedance measurements may thus be of any type that properly transfers electrical signals (via alternating current, preferably) to record any signal degradation as a result of unseen tooth surface degradation. Thus, detection of sub-crown dental caries may be performed by placing at least one probe electrode in electrical contact with a conductive port present on the surface of a target patient's properly configured crown, placing a second electrode in electrical contact with another part of the body of the patient (preferably within the patient's oral cavity, such as with the gums or inner lining of the cheek), passing an alternating electrical current between said probe and second electrodes, and measuring the electrical impedance between the electrodes to said electrical current. The impedance level would thus provide an indication of the actual condition of the covered tooth as impedance would not appreciably decrease (or otherwise change) in relation to any other source. For this purpose, then, the impedance measurement occurs over alternating current frequencies in the range from 0.1 Hz up to 500 kHz. In practice, the preferable diagnostic procedure would involve a scan of a single frequency for ease and speed of actual implementation. However, due to crown or other material changes (if, for example, overall uniformity in construction and/or material constituents is not achieved) a scan over a range of frequencies (within this broadly listed range) may be necessary to for the overall underlying tooth status diagnosis. Preferred types of probe electrodes for this purpose include those comprising a substrate of electrically insulating material, with one electrode or an electrode array patterned with electrically conductive material on at least one surface of said substrate. Preferably, the substrata of such electrode types include a generally planar, flexible, hydrophobic material, preferably polytetrafluoroethane, as one non-limiting example, that can properly hold the electrode in place when temporarily attached to a crown surface or other patient body surface. For the electrically conductive electrode, the base material is preferably carbon impregnated PTFE (with the carbon providing the needed percolation capability), again, as a non-limiting example. Other examples would thus include corrosion-resistant metal or carbon monoliths or fibers alone, again, as non-limiting examples.

The electrodes may take the form of bands or disks, and are adapted for connection to the measurement circuit of a caries detection system either individually, collectively or in predetermined groups. The substrate is preferably connected to a holder/contact means, adapted to provide electrical connection between said electrodes and a measurement circuit, particularly when applied to both the crown port and the part of the patient's body. In one embodiment, the substrate is tapered in transverse cross-section and includes a tapered core portion of compressible material, electrodes being provided on both opposite surfaces of said substrate.

Preferably, said plurality of electrodes are arranged in an array on said substrate. Most preferably, the width or diameter of said electrodes and the spacing between adjacent electrodes is in the range 0.5 to 2000 microns.

In this manner, then, the overall device provides a means to apply alternating electrical current through a conductive crown port through the interior portions of the crown/tooth composite to the dentin layer of the covered tooth to allow for the measurement of tooth surface modifications through the potential of decreased or altered electrical impedance levels in relation thereto. The level of impedance as measured through the circuit created between the two electrodes, can be measured with the distance from the port of any tooth decay or other surface deterioration indicating the rough location, at least, of such a problem location on or within the subject tooth's dentin. Importantly, it should be understood by the ordinarily skilled artisan within the pertinent technological area that the impedance across an intact crown may not be the same (or even roughly comparable) to that of a native/uncrowned tooth. As such, in practice, it is expected that a target crown will actually exhibit an impedance threshold (e.g. an absolute number) which will provide a base measurement from which underlying tooth decay may then be diagnosed in relation to the sub-threshold values such an underlying decayed tooth will provide. With an intact tooth, then, the impedance values will be significantly higher, leaving the potential for assessment of underlying tooth status in relation to an exclusive set of impedance values based on a high value correlating to an intact/healthy tooth and a lower value indicating a decaying tooth. Additionally, small changes in impedance over time may be measured to provide effective tracking methods for proper diagnosis as consistently and continuous decreasing impedance measurements will most likely reflect a decaying tooth and relatively static measurements will reflect a healthy tooth.

Likewise, with the inclusion of a proper salt or other material that would suffer demineralization in the presence of an acidic environment (and thus in the presence of colonizing bacteria), such a device could measure the overall impedance levels relating to a loss of adhesive integrity due to such a demineralization occurrence. In any event, such a device, and method, of detecting sub-crown tooth decay attributable to bacteria presence, provides unexpectedly effective and reliable results for such needed diagnoses.

BRIEF DESCRIPTION OF THE DRAWING

The above and other aspects and advantages of the present invention will be more clearly understood from the following detailed description taken in conjunction with the accompanying drawings in which:

FIG. 1 is a cross-sectional depiction of the overall inventive device including a tooth covered with a crown and to which an electrode has been applied.

DETAILED DESCRIPTION OF THE DRAWING AND PREFERRED EMBODIMENTS

Hereinafter, preferred embodiments of the present invention will now be described with reference to the accompanying drawing. Such descriptions and not intended to limit the scope of the overall invention but only to provide one potential embodiment thereof.

In the accompanying FIG. 1, a base tooth 20 (here a rough representation of a molar; it should be evident that any type of tooth to which a crown may be applied, as well as any portion of a tooth, such as a tooth post, may be utilized as the base for such a purpose) is present within a patient's gingiva 22. Applied over the tooth surface 24 is a layer of adhesive/dental cement 26, in this preferred embodiment made from a formulation of methacrylate adhesive (available from 3M, Maplewood Minn. under the tradename RelyX Unicem) with particulate calcium carbonate (available from Specialty Minerals, Bethlehem Pa. under the tradename ViCALity) mixed therein in a concentration such that the percolation threshold of the particulate is achieved. Such an adhesive layer 26 covers the entire portion of the base tooth 20 in this instance, although there may be situations where regions of adhesive are applied by a dental professional to accord a proper level of attachment, if desired. A crown 28 having an exterior surface 32 (as well as a body portion) made from primarily dielectric material of sufficient rigidity and strength to provide effective protection and biting capability for the target patient is provided as well. Such dielectric material may be, as discussed previously, any individual constituent or combination of materials to that effect, including, as preferred examples, zirconia and aluminum oxide. The crown 28 further includes an interior lining 30 of highly conductive material (such as, for instance, gold, silver, and the like, as merely examples; gold is preferred for its conductive nature and non-reactivity) covering the entire internal cavity surface of the crown 28 is supplied and present over the adhesive layer 26 to allow for the interior lining 30 full contact with the adhesive layer 26. Included within the crown 28 is a port component 34 (not illustrated) to permit electrode contact thereto as well. As noted above, such a port 34 is made from a highly conductive material (such as the material within the interior lining 30, as one example; additionally, such a port may be a region, implant, or plug of not only conductive metal, but also metal ion-containing materials for the same electrical conductivity levels needed for proper transfer of electrical signals therethrough to the base tooth 20) and permits electrode contact. A first probe electrode 40 is thus contacted to such a port surface 34 with an alternating current line 42 and source 44 included for a circuit to be created upon attachment of a second measuring electrode 46 to another part of the target patient's body (here the gingiva 22 in which the base tooth 20 is present). Upon initiation and operation then of the alternating current source 44, the electrical signal measured through the patient's body to the base tooth 20 occurs, with the expected level of electrical impedance to be set in relation to the standard measurements through a properly conductive network through another uncovered tooth (not illustrated). Such a calibrated starting point then allows for comparisons with the impedance measurements that would be characterized with an affected base tooth 20 upon the presence of surface anomalies attributable to decay 50 therein. Since the remaining portions of the entire crown/tooth composite through which any appreciable level of electrical signals would pass are highly conductive, any measured impedance would provide the dental professional with a reliable diagnosis that decay or other type of bacterial presence (such as the demineralization of the calcium carbonate and/or hydroxyapatite, as merely examples, within the adhesive/cement layer 24) has occurred, requiring therapeutic attention.

As such, the dental professional may employ computer software that may translate such impedance measurement data into information showing analysis of the apparent location and degree of decay (or, again, at least bacterial presence) under the crown 28 within the dentin of the base tooth 20. Coupling such information with an outline (roughly, even) of the expected tooth structure, may then permit generation of the apparent status of the level of mineralization or demineralization of the tooth dentin, and thus the surface integrity of the target tooth. The actual equivalent circuits derived will depend on the size and configuration of the electrode arrays used, as well as the general structure and configuration of the port present on and within the crown. Thus, the capability of feeding such impedance measurements into a proper computer program to provide three-dimensional illustrations of the subject tooth may provide an effective map of the dental caries within the covered tooth, permitting reliable diagnosis of the health status of the covered tooth without any need to remove the crown therefrom. Overall, such a device and method thus provides never before achieved capabilities at determining covered tooth conditions in a noninvasive, effective, and reliable manner.

While the invention has been shown and described with reference to a certain preferred embodiment thereof, it will be understood by those skilled in the art that various changes in form and details may be made therein without departing from the spirit and scope of the invention as defined in the appended claims.

What is claimed is:

1. A method of detecting tooth surface deficiencies for a tooth covered by a crown including metal constituents therein, wherein said method includes the provision of an original tooth structure present within a target patient's oral cavity, said tooth structure having present there over a crown structure, wherein said crown structure is adhered to said tooth structure through the utilization of an adhesive, wherein said adhesive is sufficiently strong to hold said crown structure in place over said tooth structure such that the overall configuration accorded by such a crown structure to the patient is similar to the over configuration of the tooth structure prior to inclusion of such a crown structure and wherein said crown structure is rigidly adhered to said tooth structure without any noticeable and undesirable movement, and wherein said crown structure includes a port component therein that permits integration on a temporary and selective basis of an electrode in order to avoid any appreciable interference and signal degradation attributable to the metal constituents of said crown; said method further including the integration of an electrode within said port on one end and contact with another part of the target patient's body on the other end; and operating said electrode to measure the degree of electrical impedance through the underlying tooth structure such that said impedance measurements will indicate the degree and location of any demineralization or other tooth surface alteration that is associated with dental caries.

* * * * *